US00PP34521P2

(12) United States Plant Patent
Rimland

(10) Patent No.: US PP34,521 P2
(45) Date of Patent: Aug. 23, 2022

(54) ***EPIPREMNUM AUREUM* PLANT NAMED 'LEMON MERINGUE'**

(50) Latin Name: *Epipremnum aureum*
Varietal Denomination: 'Lemon Meringue'

(71) Applicant: Michael Kerry Rimland, Miami, FL (US)

(72) Inventor: Michael Kerry Rimland, Miami, FL (US)

( * ) Notice: Subject to any disclaimer, the term of this patent is extended or adjusted under 35 U.S.C. 154(b) by 0 days.

(21) Appl. No.: 17/300,760

(22) Filed: Oct. 28, 2021

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 6/00; A01H 5/00; A01H 5/12
See application file for complete search history.

*Primary Examiner* — Keith O. Robinson
(74) *Attorney, Agent, or Firm* — Adrienne Love

(57) ABSTRACT

A new and distinct *Epipremnum aureum* cultivar named 'Lemon Meringue' is disclosed, characterized by variegated leaves with two monochromatic colors where the outer portion of the leaves are moderate yellow color and defined green central areas of the leaves extend from either side of the midrib. The new variety is an *Epipremnum aureum*, normally produced as an ornamental plant.

3 Drawing Sheets

Latin name of the genus and species of the plant claimed: *Epipremnum aureum.*

Varietal denomination: 'Lemon Meringue'.

CROSS-REFERENCES TO RELATED APPLICATIONS

None.

STATEMENT REGARDING FEDERALLY SPONSORED RESEARCH OR DEVELOPMENT

None.

BACKGROUND OF THE INVENTION

The present invention relates to a new and distinct cultivar of *Epipremnum*, botanically known as *Epipremnum aureum*, and hereinafter referred to by the name 'Lemon Meringue'.

The new *Epipremnum* plant cultivar was discovered and selected by Michael K. Rimland from a naturally occurring, single plant mutation of *Epipremnum* within a population of *Epipremnum* plants in a controlled plant nursery in Miami, Fla., U.S. Asexual reproduction of the 'Lemon Meringue' by vegetative cuttings was first performed in August 2020 in Miami, Fla. U.S. and has shown that the unique features of this cultivar are stable and reproduced to true to type in successive generations of asexual reproduction.

SUMMARY OF THE INVENTION

The cultivar 'Lemon Meringue' has not been observed under all possible environmental conditions. The phenotype may vary somewhat with variations in environment such as temperature, day length, and light intensity without, however, any variance in genotype.

The following traits have been repeatedly observed and are determined to be the unique characteristics of 'Lemon Meringue'. These characteristics in combination distinguish 'Lemon Meringue' as a new and distinct *Epipremnum aureum* cultivar:

1. Yellow variegation on outer portion of leaves with defined green area of varying shape and size in center of each leaf extending from either side of the midrib.

Plants of 'Lemon Meringue' can be compared to plants of the species selection, *Epipremnum aureum*. However, 'Lemon Meringue' differs from the plants of the mutation species selection in the following characteristics:

1. Plants of 'Lemon Meringue' produced variegated leaves that have two colors, where the moderate yellow color is on the outer portion of the leaves and the green color extends from either side of the midrib in the central portion of the leaves.

BRIEF DESCRIPTION OF THE PHOTOGRAPHS

The colored photographs herein illustrate the overall appearance of the new *Epipremnum* showing the colors as true as it is reasonably possible to obtain in color reproductions of this type. Colors in the photograph may differ slightly from the color values cited in the detailed botanical description of the new variety which accurately describes the colors of the new *Epipremnum* plant.

DETAILED BOTANICAL DESCRIPTION OF THE NEW VARIETY

Figure 1:
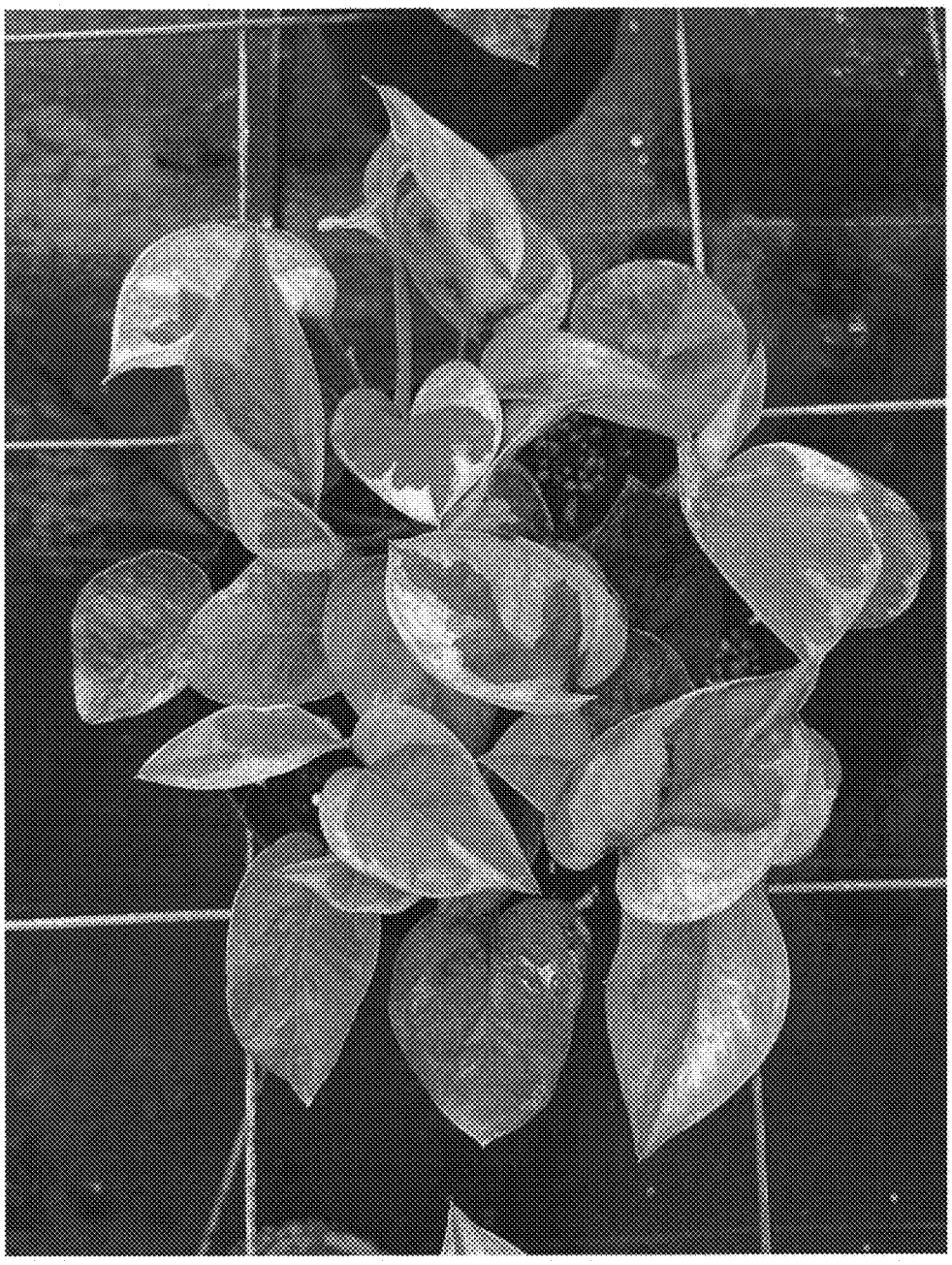
FIG. 1 is a perspective top view of a typical plant of 'Lemon Meringue', grown in a 15.24 cm diameter container.
Figure 2:
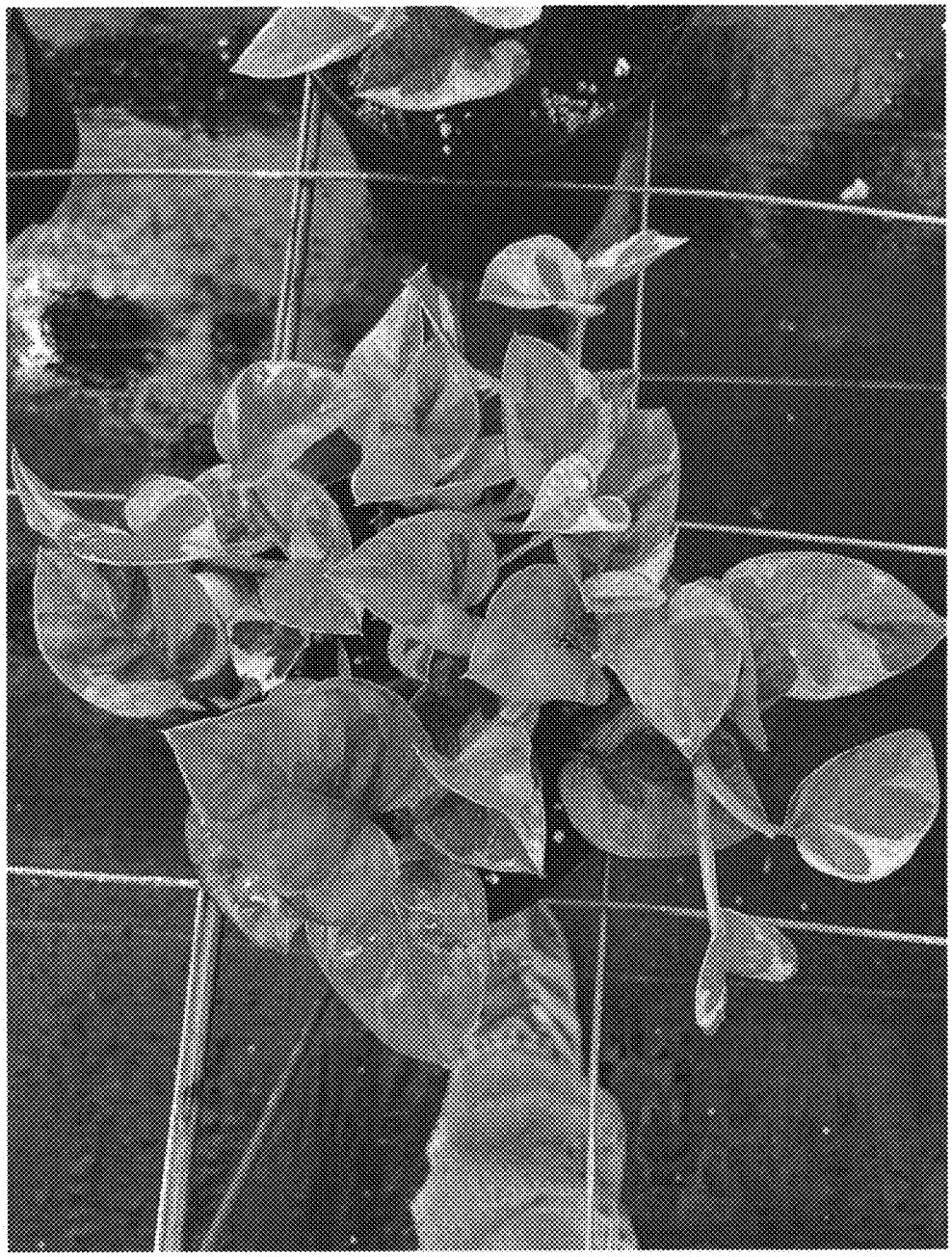
FIG. 2 is a perspective top view of a typical foliar variegation of 'Lemon Meringue', illustrating the variegation of the leaves.
Figure 3:
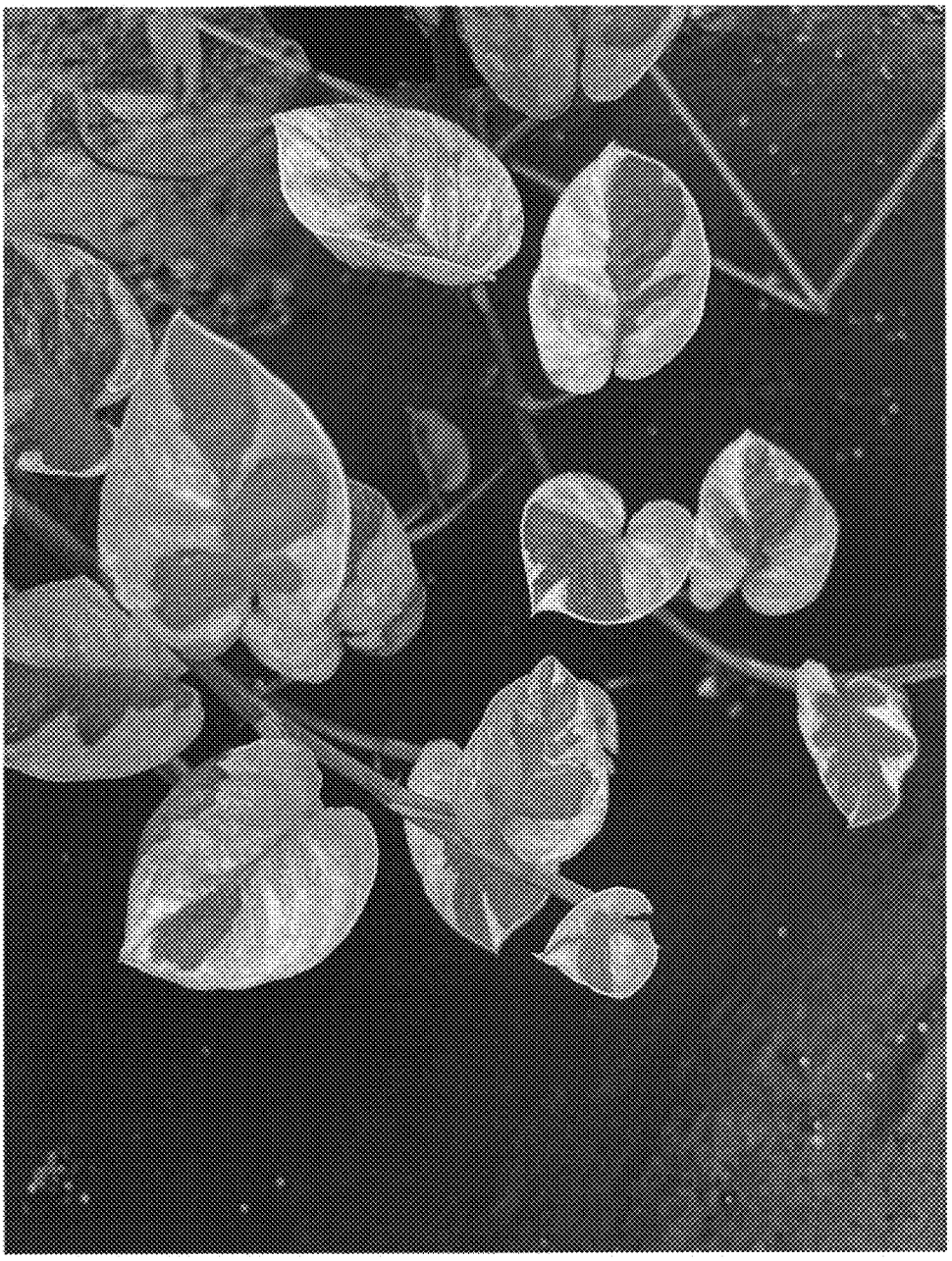
FIG. 3 is a enlarged view of a typical foliar variegation of 'Lemon Meringue', illustrating the variegation of the leaves.

The aforementioned photographs and the following observations, measurements, and values describes plants of the new *Epipremnum* grown in Miami, Fla. (U.S.) in conditions of 63% shading and 24 hr ventilation all year around in 6 inch containers and under cultural practices of commercial *Epipremnum* production. During the production of the plants, temperatures ranged from about 60 (winter)-90 (highest in summer) degrees Fahrenheit and light levels were normal sunlight. Plants were growing about 10 weeks when the photographs and the description were taken.

The following is a detailed description of the new plant characteristics with color in terminology in accordance with The Royal Horticultural Society Colour Chart, Edition V (2007), except where ordinary dictionary significance of color is indicated.

Botanical classification: *Epipremnum aureum*.

Common name: 'Lemon Meringue'.

Propagation

Type: By leaf and eye cuttings.

Time to initiate roots, summer: About 2 weeks at temperatures of 78 degrees to 90 degrees Fahrenheit.

Time to initiate roots, winter: About 3 weeks at temperatures of 60 degrees to 65 degrees Fahrenheit.

Time to produce a rooted young plant, spring: About 4 weeks at temperatures of 80 degrees to 90 degrees Fahrenheit.

Root description: Thick and dense; fleshy when plants mature; typical of species.

Plant

Growth habit: Low growing, cascading.

Plant shape: Plants are full, compact and have dense foliage.

Height (from soil level to top of leaf plane): Approximately 15 cm to top of highest leaf.

Plant diameter or spread: Approximately 152 mm.

Growth rate: Rapid.

Stem description:

*Length*.—About 203 mm.

*Diameter*.—About 2 mm.

*Internode length*.—About 50 mm.

*Texture*.—Smooth.

*Branching*.—Stems do not tend to branch.

*Colors, mature*.—Moderate yellow green 154C and green N144C.

Age of plant described: Approximately 10 weeks.

Foliage

Leaves:

*Leaf*.—Ovate, egg shape, rounded base, apex is pointy. Smooth texture on top surface and bottom surface. Margin is entire, without serration.

*Arrangement*.—Alternate.

*Average length*.—About 8 inches.

*Average width*.—About 6 inches

*Shape of blade*.—Ovate, egg shape.

*Apex*.—Acuminate, pointy.

*Base*.—Rounded.

*Attachment*.—Stalked.

*Leaf internode length*.—Approximately 2.4 cm.

*Color*.—Mature leaves, upper surface: Centered variegation, areas of moderate yellow green 154C and green N144C; Mature leaves, lower surface: primary color moderate yellow green 154C and secondary color of green N144C.

*Venation*.—Reticulate, with lower surface venation color green N144C.

Petiole:

*Length*.—50 mm.

*Diameter*.—About 2 to 3 mm.

*Strength*.—Strong.

*Texture*.—Smooth.

*Color*.—Moderate yellow green 154C.

Flower

Blooming not observed on the new cultivar.

Other Characteristics

Seed production: No seed production to date has been observed.

Temperature tolerance: Normal tropical conditions. Tolerant up to and including USDA Zone 10a.

Other distinctive characteristics: Overall commercially interesting appearance. When compared to its closest comparison cultivar 'Global Green', disclosed in U.S. Plant Pat. No. 33,530, respectively, 'Lemon Meringue' differs in the following characteristics:

1. 'Lemon Meringue' has a primary color on its leaf of moderate yellow green 154C that contrasts with its secondary color of green N144C. Whereas, 'Global Green' has a leaf with a primary color of moderate olive-green 137A that contrasts with its secondary color of moderate yellow green 137A.
2. 'Lemon Meringue' has yellow variegation on outer portion of leaves with defined green area of varying shape and size in center of each leaf extending from either side of the midrib. Whereas, 'Global Green' has moderate yellow green in the central variegated area of its leaves and moderate olive-green on the outer variegated area of its leaves.

What is claimed is:

1. A new and distinct cultivar of *Epipremnum aureum* plant named 'Lemon Meringue' as illustrated and described.

* * * * *